United States Patent [19]
Kleemann

[11] Patent Number: 5,840,654
[45] Date of Patent: Nov. 24, 1998

US005840654A

[54] HERBICIDAL HETEROCYCLIC-SUBSTITUTED PYRIDINES

[75] Inventor: Alex Kleemann, Hanau, Germany

[73] Assignee: American Cyanamid Company, Madison, N.J.

[21] Appl. No.: 525,690

[22] PCT Filed: Mar. 25, 1994

[86] PCT No.: PCT/EP94/00969

§ 371 Date: Feb. 2, 1996

§ 102(e) Date: Feb. 2, 1996

[87] PCT Pub. No.: WO94/22833

PCT Pub. Date: Oct. 13, 1994

[30] Foreign Application Priority Data

Mar. 26, 1993 [EP] European Pat. Off. .............. 93105006

[51] Int. Cl.$^6$ .......................... A01N 43/40; C07D 401/12
[52] U.S. Cl. ..................... 504/251; 504/253; 546/268.1; 546/276.1
[58] Field of Search .............................. 546/268.1, 276.1; 504/251, 253

[56] References Cited

U.S. PATENT DOCUMENTS

| | | | |
|---|---|---|---|
| 3,535,328 | 10/1970 | Zielinski | 260/296 |
| 3,687,959 | 8/1972 | Zielinski | 260/295 |
| 4,046,553 | 9/1977 | Takahashi et al. | 71/94 |
| 4,213,774 | 7/1980 | Schurter et al. | 71/94 |
| 4,267,336 | 5/1981 | Nishiyama et al. | 546/302 |
| 4,309,547 | 1/1982 | Koch et al. | 546/301 |
| 4,317,913 | 3/1982 | Cartwright | 546/345 |
| 4,324,627 | 4/1982 | Cartwright | 204/158 HA |
| 4,325,729 | 4/1982 | Rempfler et al. | 71/94 |
| 4,493,730 | 1/1985 | Kimura et al. | 71/94 |
| 5,155,113 | 10/1992 | Fujii | 514/274 |
| 5,374,604 | 12/1994 | Kleeman et al. | 504/130 |

FOREIGN PATENT DOCUMENTS

| | | |
|---|---|---|
| 0 109 751 | 10/1983 | European Pat. Off. . |
| 0 371 947 | 11/1983 | European Pat. Off. . |
| 63-250324 | 10/1988 | Japan . |

OTHER PUBLICATIONS

CA Registry No.: 142802–49–1; 142802–50–4; 142802–51–5; 142802–52–6; 141212–69–3; 139140–52–6; 129452–57–9; 129452–27–3; 12620907–2; 126209–12–9; 96591–92–3; and 94377–81–2, CAS Registry Handbook, 1992.

J. Med. Chem 10, 320–325, Mertes et al., Approaches to ... deazauridine, 1996.

CA 113: 132173v Pyrazole ... Active Ingredients. Haga et al., p. 652, 1990.

CA 116: 106314; Preparation ... Fungicides. Ohsumi et al., p. 781, 1992.

*Primary Examiner*—Joseph McKane
*Attorney, Agent, or Firm*—Joseph M. Mazzarese

[57] ABSTRACT

The present invention relates to 2,6-substituted pyridines of formula I, their preparation and use as herbicides.

16 Claims, No Drawings

HERBICIDAL HETEROCYCLIC-SUBSTITUTED PYRIDINES

This application is a 371 of PCT/EP94/00969 filed Mar. 25, 1994.

The present invention is concerned with certain 2,6-substituted pyridines, their preparation and use as herbicides.

Pyridines and pyridine derivatives have many uses, for example, as pharmaceuticals, pesticides (herbicides, acaricides, anthelmintics, bird repellants), feed supplements, solvents, reagents, intermediates, and chemicals for the polymer and textile industry. Various 2,6-diaryloxy- or -diarylmethoxy-pyridine derivatives have been investigated for such uses, the compounds often having additional substitution of the central pyridine ring.

The dibenzyloxy analogue of 2,6-diphenoxy-pyridine, in addition to being mentioned in JP-A-63250324, EP-A-180188 and J. Med. Chem, 10(2), pages 320 to 325, all medical research publications, was prepared as an example of the herbicidal compounds proposed in U.S. Pat. No. 3,535,328 and the divisional published as U.S. Pat. No. 3,687,959. Both texts are predominantly directed to the herbicidal, fungicidal, and, for the compounds claimed in U.S. Pat. No. 3,535,328, nematocidal and insecticidal activity, of amido or aminothioethoxy derivatives. No herbicidal activity data is given for the disclosed 2,6-dibenzyloxypyridine.

Applicants copending European Patent Applciation 92304795, filed 27th May 1992, (ref. T.1632 EPC) describes how certain substituted forms of 2,6-diphenoxypyridine and 2,6-dibenzyloxypyridine, and also the related asymmetric 2-phenoxy-6-benzyloxy pyridines, have a spectrum of herbicidal activity significantly different from the unsubstituted analogues in possessing post-emergence action against both grass-type plants and also broadleaf plants. Certain of those compounds are known per se, and said application claims their herbicidal application.

It has now been found, and forms the subject of the present invention, that good herbicidal activity is also present in related, novel pyridine derivatives having nitrogen-containing heteroaromatic substituents. In one embodiment, the present invention therefore provides 2,6-substituted pyridines of the formula I:

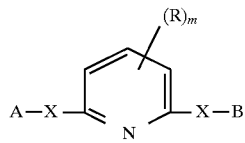

wherein X represents an oxygen or sulphur atom; A represents an optionally substituted 5 or 6 membered nitrogen-containing heteroaromatic group; B represents an optionally substituted 5 or 6 membered cyclic hydrocarbon, alkyl, alkenyl, alkynyl, aryl or aralkyl group, or one of the meanings for A; R represents a halogen atom or an alkyl, haloalkyl, alkoxy, alkylthio or dialkylamino group; and m represents 0, 1 or 2.

Group A is suitably pyridyl, especially 4-pyridyl or pyrazolyl, especially 5-pyrazolyl, and group B is suitably one of such groups, or phenyl or benzyl. The groups A and B may be the same or different, and are preferably substituted, in particular having a substituent at the meta position (except for B-benzyl). The substituent groups may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds. There may be one or more of the same or different substituents present in each radical.

Optional substituents in groups A and/or B include halogen atoms and nitro, cyano, alkyl, haloalkyl, alkoxy, alkylthio and aryl groups. Preferred substituents are a halogen, especially chlorine, atom, or an alkyl or haloalkyl group of 1 to 6 carbon atoms.

An alkyl group, either as a substituent on one or other of groups A and B, or as group R, may have a straight or branched chain, suitably containing up to 12, preferably 1 to 6, carbon atoms. In a haloalkyl group, whether as a substituent on one or other of groups A and B, or as group R, the halogen atom may be one or more fluorine, chlorine, bromine or iodine atoms, with fluorine being preferred and trifluoromethyl the preferred haloalkyl group.

Preferred compounds are those wherein each X represents an oxygen atom and m is 0 or 1.

The compound of formula I wherein X is oxygen may be prepared by appropriate adaptation of conventional methods of obtaining substituted pyridine compounds, the basic technique being, for example, reaction of a metal salt of the appropriate alcohol with an appropriate 2,6-dihalopyridine, in a solvent and suitably at elevated temperature, ideally at reflux. For the preparation of symmetrical pyridine compounds, the reaction can be carried out in one step by using a molar ratio of alcohol salt to pyridine of at least 2:1. For asymetrical compounds of formula I, separate introduction of the two substituents is required in a two-stage process.

The present invention therefore provides, in a further embodiment, a process for the preparation of a compound of formula I wherein A and B are the same, which comprises reacting a 2,6-dihalopyridine of formula II

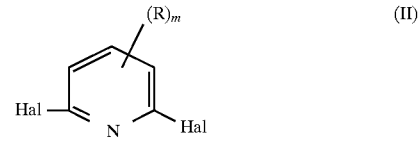

with at least a twofold molar excess of a metal salt of an alcohol or thiol of formula AXH, the symbols A, X, R and m being as defined in relation to formula I and Hal denoting a halogen, preferably chlorine or bromine, atom.

When group B in formula I is different from group A, the 2,6-dihalopyridine of formula II above is first reacted with at most an equimolar amount of a metal salt of an alcohol or thiol of formula AXH, followed by further reaction with at least an equimolar amount of a metal salt of an alcohol or thiol of formula BXH.

An alternative, and preferred, process for the preparation of compounds of formula I where B is different from A comprises reacting a halopyridone of formula III

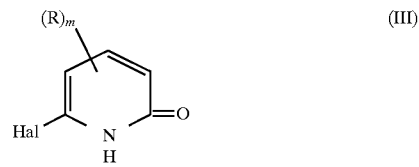

with a halide of formula BHal, wherein each Hal denotes a halogen, suitably bromine, atom, followed by reaction with a metal salt of an alcohol or thiol of formula AXH. The first stage of this reaction is conveniently carried out by reacting the pyridone of formula III with an alkali metal hydroxide to form the pyridoyxlate salt, which is then reacted with the halide BHal, preferably in a solvent such as dimethylformamide.

Either of the above reactions is conveniently carried out in an organic solvent, the selection of which is dependent on the precise nature of the reactants involved. Generally any polar organic solvent is suitable, for example dimethylformamide and tetrahydrofuran.

The metal salt of the alcohol or thiol is preferably an alkali metal salt, for example a sodium or potassium salt, and is conveniently generated by reaction of the alcohol with a suitable metal base, for example a metal carbonate or hydride.

The prepared compounds of formula I may, if desired, be isolated and purified using conventional techniques.

Compounds of general formula II, and the alcohols/thiols of formula BXH are generally known and/or are easily preparable by standard techniques.

Compounds of the general formula I have been found to have interesting activity as herbicides having a wide range of pre- and post-emergence activity against undesirable species.

The present invention therefore provides a herbicidal composition which comprises a compound of the present invention in association with a carrier.

The present invention additionally encompasses the preparation of such a herbicidal composition by the process of bringing a carrier into association with a compound of the present invention.

Preferably there are at least two carriers in a composition of the present invention, at least one of which is a surface-active agent.

The present invention further provides the use of a compound according to the invention as a herbicide.

Further, in accordance with the invention there is provided a method of combating undesired plant growth at a locus by treating the locus with a composition or compound according to the invention. The locus may, for example, be the soil or plants in a crop area. Application to the locus may be pre-emergence or post-emergence. The dosage of active ingredient used may, for example, be from 0.01 to 10 kg/ha, preferably 0.01 to 4 kg/ha.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ether; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The herbicidal composition of the invention may also contain other biologically active ingredients, for example compounds possessing herbicidal, insecticidal or fungicidal properties.

The following Examples illustrate the invention. The structures of the compounds of the invention prepared in the following Examples were confirmed by mass spectrometry and NMR.

EXAMPLE 1

Preparation of 2,6-di-(2'-chloropyrid-4'-yloxy)pyridine

A mixture of 11.8 g 2,6-dibromopyridine, 13 g 2-chloro-4-hydroxypyridine and 13.8 g potassium carbonate in 20 ml N,N-dimethylformamide was heated to reflux for 12 hours. After cooling, 150 ml of water was added and the aqueous layer extracted three times each with 100 ml ethyl acetate. The combined extracts were dried with anhydrous magnesium sulphate. The solvent was evaporated and the resulting brown oil purified by flash silica gel column chromatography using hexane/ethyl acetate 7/3. The title compound was obtained as a pale brown solid, mp 95° C. Analysis. Calc. C 53.9; H 2.7; N 12.6%, Found: C 53.7; H 3.0; N 12.4%

EXAMPLE 2

A) Preparation of 2-bromo-6-(1'-methyl-3'-trifluoromethylpyrazol-5'-yloxy)-pyridine A mixture of 14.3 g 2,6-dibromopyridine, 10 g 1-methyl-3-trifluoromethyl-5-hydroxypyrazole and 8.3 g potassium carbonate in 20 ml N,N-dimethylformamide was refluxed for 4 hours. The reaction mixture then was allowed to cool to ambient temperature and 150 ml of water was added. The aqueous layer was extracted three times each with 100 ml ethyl acetate. The combined extracts were dried with anhydrous magnesium sulphate and the solvent evaporated in vacuo. Purification of 2-bromo-6-(1'-methyl-3'-trifluoromethylpyrazol-5'-yloxy)pyridine by flash silica gel column chromatography using hexane/ethyl acetate 8/2 gave a white solid, mp 53° C.

B) Preparation of 2-(1'-methyl-3'-trifluoromethylpyrazol-5'-yloxy)-6-(3"-trifluoromethylphenoxy)pyridine 1.6 g of the monosubstituted intermediate, prepared as described above, 0.6 ml of 3-hydroxybenzotrifluoride and 0.7 g potassium carbonate were mixed with 2 ml N,N-dimethylformamide and heated to reflux for 12 hours. After cooling 50 ml water was added and the mixture extracted three times each with 50 ml ethyl acetate. The combined extracts were dried with anhydrous magenesium sulphate, the solvent evaporated and the crude product purified by flash silica gel column chromatography using hexane/ethyl acetate 9/1. The title compound was obtained as a pale yellow oil. Analysis: Calc. C 50.6; H 2.7; N 10.4%, Found: C 50.8; H 2.7; N 10.6%.

EXAMPLE 3

A) Preparation of 2-bromo-6-benzyloxypyridine 2.9 ml benzyl alcohol was dissolved in 10 ml N,N-dimethylformamide and 0.7 g sodium hydride (purity 95%) was slowly added. After gas evolution has ceased, 6 g 2,6-dibromopyridine was added and the mixture heated to reflux for 3 hours. After cooling, the reaction mixture was filtered through a silica gel column using hexane/ethyl acetate 1/1. The solvent was removed in vacuo and the crude product purified by flash silica gel column chromatography. The title compound was obtained as a colourless oil.

B) Preparation of 2-bromo-6-(4'-fluorobenzyloxy)pyridine (alternative route)

A solution of 4.6 g 6-bromo-2-pyridone (the preparation of this compound is described in Synthesis, 707 (1974)) and 1.56 g potassium hydroxide in 20 ml methanol was prepared. The solvent was evaporated in vacuo after toluene was added to give the anhydrous potassium pyridoxylate. This was dissolved in 10 ml N,N-dimethylformamide, 3.7 ml 4-fluorobenzyl bromide was added and the mixture heated to reflux for 2 hours. After cooling, 100 ml of water was added and the aqueous layer extracted three times with ethyl acetate. The combined extracts were dried with anhydrous magnesium sulphate and the solvent removed in vacuo. The residue was purified by flash silica gel column chromatography using hexane/ethyl acetate 95/5. The title compound was obtained as a white solid (3.3 g, 44%) of melting point 82° C.

C) Preparation of 2-(2'-chloropyrid-4'-yloxy)-6-benzyloxypyridine

To a solution of 0.65 g 2-chloro-4-hydroxypyridine in 10 ml N,N-dimethylformamide, 0.13 g sodium hydride was added slowly. After gas evolution had ceased, 1.2 g 2-bromo-6-benzyloxypyridine (prepared as described in A) above) was added and the mixture heated to reflux for 30 hours. After cooling, the reaction mixture was filtered through a silica gel column using hexane/ethyl acetate 4/1. The solvent was evaporated in vacuo and the crude product purified by flash silica gel column chromatography using hexane/ethyl acetate 9/1. The title compound was obtained as a yellow oil. Analysis. Calc: C 65.3; H 4.2; N 9.0%, Found. C 65.2; H 3.9; N 9.1%.

EXAMPLE 4–8

Following procedures analogous to one or other of those described in Examples 1–3, further compounds of the invention were prepared whose details are given below in Table I. In that Table, the structure of each compound is identified by reference to the substituents in formula IV below.

A—O—[pyridine]—O—B  (IV)

| Ex. No. | A | B | M. Pt. °C. | Analysis Calc/Found C | H | N |
|---|---|---|---|---|---|---|
| 4 | CH₃-pyrazole-CF₃ | —CH₂Phenyl | Oil (nmr) | 58.4 / 58.0 | 4.0 / 3.7 | 12.0 / 11.9 |
| 5 | CH₃-pyrazole-CF₃ | CH₃-pyrazole-CF₃ | 111 | 44.2 / 44.3 | 2.7 / 2.8 | 17.2 / 16.7 |
| 6 | 2-Cl-pyridyl | 3-CF₃-phenyl | Oil (nmr) | 55.7 / 55.7 | 2.7 / 2.5 | 7.6 / 7.3 |
| 7 | CH₃-pyrazole-CF₃ | 2-Cl-pyridyl | Oil (nmr) | 48.6 / 48.7 | 2.7 / 2.8 | 15.1 / 14.9 |

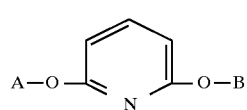

(IV)

| Ex. No. | A | B | M. Pt. °C. | Analysis Calc/Found | | |
|---|---|---|---|---|---|---|
| | | | | C | H | N |
| 8 | 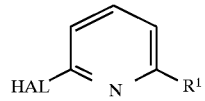 | Phenyl | oil (nmr) | 64.3 64.2 | 3.7 3.7 | 9.4 9.2 |

For those compounds of formula I described above which were obtained as oils, the relevant nmr data (ppm in $CDCl_3$ solution) are listed below in Table II.

TABLE II

| Compound of Ex. No. | Nmr characteristics |
|---|---|
| 2 | 3.68 (s, $CH_3$ group); 5.84 (s, 1H); 6.73 (d, 1H); 6.80 (d, 1H); 7.22–7.34 (m, 2H); 7.46–7.51 (m, 2H); 7.79 (t, 1H). |
| 3 | 5.19 (s, 2H-benzylic); 6.62 (dd, 1H); 6.88 (dd, 1H); 7.05 (d, 1H); 7.23–7.37 (m, 6H); 7.65 (t, 1H); 8.22 (d, 1H). |
| 4 | 3.67 (s, $CH_3$-group); 5.18 (s, 2H-benzylic); 6.20 (s, 1H); 6.56 (d, 1H); 6.62 (d, 1H); 7.23–7.40 (m, 5H); 7.66 (t, 1H). |
| 6 | 6.75 (d, 1H); 6.89 (dd, 1H); 7.02 (d, 1H); 7.29 (m, 2H); 7.36 (s, 1H); 7.83 (t, 1H); 8.19 (d, 1H). |
| 7 | 3.72 (s, $CH_3$-group); 6.12 (s, 1H); 6.81–6.89 (m, 2H), 6.92–6.97 (m, 1H); 7.08 (d, 1H); 7.88 (t, 1H); 8.29 (d, 1H). |
| 8 | 6.66 (d, 1H); 6.69 (d, 1H); 6.93 (dd, 1H); 7.08 (d, 2H); 7.12–7.22 (m, 2H); 7.31–7.39 (m, 2H); 7.75 (t, 1H); 8.18 (d, 1H). |

EXAMPLE 9

Preparation of 2-Fluoro-6-(1'-methyl-3'-trifluoromethylpyrazol-5'-yloxy)pyridine To a mixture of 4.54 ml (0.05 mol) 2,6-difluoropyridine in 100 ml of anhydrous N,N-dimethylformamide and 7.6 g (0.055 mol) potassium carbonate was added 9.3 g (0.05 mol) of 1-methyl-3-trifluoromethyl-5-hydroxyzole in one gram portions while heating the mixture to reflux for 4 hours. The time intervals between the portions were 15 minutes.

After cooling the solvent was removed in vacuo and the residue suspended in 200 ml ethyl acetate. The organic layer was washed with 100 ml water, separated, and the solvent was removed in vacuo.

Flash silica gel column chromatography using hexane/ethyl acetate 8/2 afforded 5 g (38%) of a yellow oil.

EXAMPLES 10 TO 16

By methods analogous to that of Example 9, the following intermediates of the general formula XX have been prepared (table II):

TABLE II

HAL—N—$R^1$ (pyridine structure)

| Example No | $R^1$ |
|---|---|
| 10 | 1',3'-dimethylpyrazol-5'-yloxy |
| 11 | 1'-methyl-3'-tert.-butylpyrazol-5'-yloxy |
| 12 | 1'-methyl-3'-ethylpyrazol-5'-yloxy |
| 13 | 1'-methyl-3'-isopropylpyrazol-5'-yloxy |
| 14 | 1'-ethyl-3'-trifluoromethylpyrazol-5'-yloxy |
| 15 | 2'-chloropyrid-4'-yloxy |
| 16 | 3'chloropyrid-5'-yloxy |

EXAMPLE 17

Preparation of 2-(1'-methyl-3'-trifluoromethylpyrazol-5'-yloxy)-6-phenoxypyridine A mixture of 1.31 g (0.005 mol) 2-Fluoro-6-(1'-methyl-3'-trifluoromethylpyrazol-5'-yloxy)pyridine (prepared as described in Example 9), 0.51 g phenol (0.0055 mol) and 0.76 g (0.0055 mol) potassium carbonate in 3 ml N,N-dimethylformamide was heated to reflux for 1 hour. After cooling, the mixture was poured in 20 ml water, and the aqueous layer was extracted three times with each 20 ml ethyl acetate. The combined extracts were dried with anhydrous magnesium sulphate. The solvent was evaporated and the residue purified by a flash silica gel column chromatography using hexane/ethyl acetate 8/2. The title compound was obtained as a white solid (1.1 g, 66%) of melting point 78°.

EXAMPLES 18 TO 56

By methods analogous to that of Example 17, the compounds of the general formula XX listed in table IIIa were prepared starting from intermediataes of the general formula XX prepared as described in Examples 9 to 16.

TABLE IIIa

| Example No. | R¹ | R² | mp (°C.) | yield (%) |
|---|---|---|---|---|
| 18 | 1'-Me-3'-CF₃-pyrazol-5'-yloxy | cyclopentyloxy | oil | 36 |
| 19 | 2'-chloropyrid-4'-yl | phenyloxy | oil | 14 |
| 20 | 2'-chloropyrid-4'yl | 3"-CF₃-4"-fluorophenyloxy | 71 | 29 |
| 21 | 2'chloropyrid-4'-yl | 2"-fluorophenyloxy | 79 | 32 |
| 22 | 1'-Me-3'-CF₃-pyrazol-5'-yloxy | 4"-fluorophenyloxy | 95 | 25 |
| 23 | 1'-Me-3'-CF₃-pyrazol-5'-yloxy | 2"-fluorophenyloxy | 104 | 54 |
| 24 | 1'-Me-3'-CF₃-pyrazol-5'-yloxy | 2",4"-difluorophenyloxy | 98 | 58 |
| 25 | 1'-Me-3'-CF₃-pyrazol-5'-yloxy | 2"-methylphenyloxy | oil | 40 |
| 26 | 1'-Me-3'-CF₃-pyrazol-5'-yloxy | 2"-pyridyloxy | 135 | 42 |
| 27 | 1'-Me-3'-CF₃-pyrazol-5'-yloxy | 3"-chloropyrid-5"-yloxy | oil | 32 |
| 28 | 1'-Me-3'-CF₃-pyrazol-5'-yloxy | 2"-chloropyrid-6"-yloxy | oil | 27 |
| 29 | 1'-Me-3'-CF₃-pyrazol-5'-yloxy | 3"-fluorophenyloxy | 66 | 51 |
| 30 | 1'-Me-3'-CH₃-pyrazol-5'-yloxy | 3"-CF₄-4"-fluorophenyloxy | oil | 29 |
| 31 | 1'-Me-3'-Me-pyrazol-5'-yloxy | 1'-Me-3'-Me-pyrazol-5'-yloxy | oil | 49 |
| 32 | 1'-Me-3'-CF₃-pyrazol-5'-yloxy | 1"-Me'-3"-pyrazol-5"-yloxy | 85 | 73 |
| 33 | 1'-Me-3'-t-Butyl-pyrazol-5'-yloxy | 1"-Me-3"-Me-pyrazol-5"-yloxy | oil | 50 |
| 34 | 1'-Me'3'-t-Butyl-pyrazol-5'-yloxy | 1"-Me-3"-i-propyl-pyrazol-5"-yloxy | oil | 90 |
| 35 | 1'-Me-3'-CF₃-pyrazol-5'-yloxy | 1"-Me-3"-t-Butyl-pyrazol-5"-yloxy | oil | 85 |
| 36 | 1'-Me-3'-Me-pyrazol-5'-yloxy | 1"-Me-3'-i-propyl-pyrazol-5"-yloxy | oil | 36 |
| 37 | 1'-Me-3'-Ethyl-pyrazolyl-5'-yloxy | 1'-Me-3'-Ethyl-pyrazolyl-5'-yloxy | oil | 18 |
| 38 | 1'Me-3'-CF₃-pyrazol 5'-yloxy | 1"-Me-3"-i-propyl-pyrazol-5"-yloxy | oil | 42 |
| 39 | 1'-Me-3'--i-propyl-pyrazolyl-5'-yloxy | 1'-Me-3'-1-propyl-pyrazolyl-5'-yloxy | oil | 44 |
| 40 | 1'-Me-3'-t-Butyl-pyrazol-5'-yloxy | 1'-Me-3'-t-Butyl-pyrazol-5'-yloxy | oil | 33 |
| 41 | 1'-Me-3'-t-Butyl-pyrazol-5'-yloxy | 2"-chloropyrid-4"-yloxy | oil | 78 |
| 42 | 1'-Me-3'-t-Butyl-pyrazol-5'-yloxy | 4"-fluorophenyloxy | oil | 82 |
| 43 | 1'-Me-3'-t-Butyl-pyrazol-5'-yloxy | 3"-fluorophenyloxy | oil | 82 |
| 44 | 1'-Me-3'-t-Butyl-pyrazol-5'-yloxy | 2"-fluorophenyloxy | oil | 53 |
| 45 | 2'-chloropyrid-4'-yloxy | 2"-methylphenyloxy | oil | 32 |
| 46 | 2'-chloropyrid-4'-yloxy | 4"-fluorophenyloxy | oil | 35 |
| 47 | 2'-chloropyrid-4'-yloxy | 3"-fluorophenyloxy | oil | 36 |
| 48 | 3'-chloropyrid-5'-yloxy | 3'-chloropyrid-5'-yloxy | 62 | 54 |
| 49 | 1'-Me-3'-CF₃-pyrazol-5'-yloxy | 3",4"-dimethylphenyloxy | 88 | 70 |
| 50 | 1'-Me-3'-CF₃-pyrazol-5'-yloxy | 3"-methyl-4"-chlorophenyloxy | 52 | 41 |
| 51 | 1'-Me'3'-CF₃-pyrazol-5'-yloxy | 3"-methyl-4"-nitrophenyloxy | 103 | 55 |
| 52 | 1'-Me-3'-CF₃-pyrazol-5'-yloxy | 3"-41"-dichlorophenyloxy | 92 | 27 |
| 53 | 1'-Me-3'-CF₃-pyrazol-5'-yloxy | 3"-CF₃-4"-chlorophenyloxy | 70 | 68 |
| 54 | 1'-Me-3'-CF₃-pyrazol-5'-yloxy | 3"-cyanophenyloxy | 91 | 71 |
| 55 | 1'-Me-3'-CF₃-pyrazol-5'-yloxy | 3"-chloro-4"-cyanophenyloxy | 95 | 16 |
| 56 | 1'-Me-3'-CF₃-pyrazol-5'-yloxy | 3"-chloro-4"-fluorophenyloxy | 76 | 65 |

Abbreviations: Me = methyl, t-Butyl = tertiary butyl, i-propyl = isopropyl, CF₃ = trifluoromethyl

EXAMPLES 57 TO 85

Following procedures analagous to Examples 17 to 48, the following compounds of the general formula XX listed in table IIIb were prepared.

TABLE IIIb

| Example No | R¹ | R² | mp (°C.) | yield (%) |
|---|---|---|---|---|
| 57 | 1'-Me-3'-CH₃-pyrazol-5'-yloxy | 3"-fluorobenzyloxy | oil | 68 |
| 58 | 1'-Me-3'-CF₃-pyrazol-5'-yloxy | 4"-fluorobenzyloxy | oil | 44 |
| 59 | 1'-Me-3'-CF₃-pyrazol-5'-yloxy | 2"-fluorobenzyloxy | oil | 33 |
| 60 | 1'-Me-3'-CF₃-pyrazol-5'-yloxy | 4"-CF₃-benzyloxy | oil | 43 |
| 61 | 1'-Me-3'-CF₃-pyrazol-5'-yloxy | 3"-CF₃-benzyloxy | oil | 38 |
| 62 | 1'-Me-3'-CF₃-pyrazol-5'-yloxy | 4"-methylbenzyloxy | oil | 39 |
| 63 | 1'-Me-3'-CF₃-pyrazol-5'-yloxy | 2"-methylbenzyloxy | oil | 39 |
| 64 | 1'-Me-3'-CF₃-pyrazol-5'-yloxy | 4"-tert.-butylbenzyloxy | oil | 35 |
| 65 | 1'-Me-3'-CF₃-pyrazol-5'-yloxy | 3"-chlorobenzyloxy | oil | 36 |
| 66 | 1'-Me-3'-CF₃-pyrazol-5'-yloxy | 3"-methylbenzyloxy | oil | 41 |
| 67 | 1'-Me-3'-CF₃-pyrazol-5'-yloxy | 2",6"-dichlorobenzyloxy | 110 | 67 |
| 68 | 1'-Me-3'-CF₃-pyrazol-5'-yloxy | α-methylbenzyloxy | oil | 50 |
| 69 | 1'-Me-3'-CF₃-pyrazol-5'-yloxy | 4"-chlorobenzyloxy | oil | 63 |
| 70 | 1'-Me-3'-CF₃-pyrazol-5'-yloxy | 2"-chlorobenzyloxy | oil | 57 |
| 71 | 1'-Me-3'-CF₃-pyrazol-5'-yloxy | 2",4"-difluorobenzyloxy | oil | 20 |
| 72 | 1'-Me-3'-CF₃-pyrazol-5'-yloxy | 2",4",5"-trifluorobenzyloxy | 68 | 20 |
| 73 | 1'-Me-3'-CF₃-pyrazol-5'-yloxy | 2",3",4"-trifluorobenzyloxy | 55 | 25 |
| 74 | 2'-chloropyrid-4'-yloxy | 4"-fluorobenzyloxy | oil | 6 |
| 75 | 1'-Me-3'-CF₃-pyrazol-5'-yloxy | α-CF₃-benzyloxy | 75 | 67 |
| 76 | 1'-Me-3'-t-butyl-pyrazol-5'-yloxy | 2"-methylbenzyloxy | oil | 51 |
| 77 | 2'-chloropyrid-4'-yloxy | 2"-fluorobenzyloxy | oil | 27 |
| 78 | 2'-chloropyrid-4'-yloxy | 3"-fluorobenzyloxy | oil | 55 |

TABLE IIIb-continued $$R^1 \diagdown N \diagdown R^2$$

| Example No | R¹ | R² | mp (°C.) | yield (%) |
|---|---|---|---|---|
| 79 | 2'-chloropyrid-4'-yloxy | 2"-methylbenzyl-oxy | oil | 52 |
| 80 | 2'-chloropyrid-4'-yloxy | 2",4"-difluoro-benzyloxy | oil | 34 |
| 81 | 1'-Me-3'-t-butyl-pyrazol-5'-yloxy | 4"-fluorobenzyl-oxy | oil | 33 |
| 82 | 1'-Me-3'-t-butyl-pyrazol-5'-yloxy | 3"-fluorobenzyl-oxy | oil | 41 |
| 83 | 1'-Me-3'-t-butyl-pyrazol-5'-yloxy | 2"-fluorobenzyl-oxy | 61 | 50 |
| 84 | 1'-Me-3'-t-butyl-pyrazol-5'-yloxy | 2",4"-difluoro-benzyloxy | oil | 22 |
| 85 | 1'-Me-3'-t-butyl-pyrazol-5'-yloxy | benzyloxy | oil | 29 |

EXAMPLES 86 TO 88

By a method analogous to that of Example 17, further compounds of the general formula XX were prepared and are listed in table IIIc.

TABLE IIIc $$R^1 \diagdown N \diagdown R^2$$

| Example No | R¹ | R² | mp (°C.) | yield (%) |
|---|---|---|---|---|
| 86 | 1'-Me-3'-CF₃-pyrazol-5'-yloxy | 1"-phenylethyloxy | oil | 39 |
| 87 | 1'-Me-3'-CF₃-pyrazol-5'-yloxy | 2"-propinyloxy | 57 | 19 |
| 88 | 1'-Me-3'-CF₃-pyrazol-5'-yloxy | tert.-butyloxy | oil | 77 |

EXAMPLE 89
Preparation of 2,6-Dibromo-4-methylpyridine

To a solution of 2-methyl-2-chloromethyloxirane (50 g; 0.47 mol) in 23 ml of concentrated hydrochloric acid) at ice-bath temperature was added a solution of sodium cyanide (27.4 g; 0.56 mol) in 23 ml of hydrochloric acid. After stirring for 10 hours at that temperature, the reaction mixture was warmed up to 40° C.

To this solution of potassium cyanide (33.8 g; 0.52 mol) in 50 ml water was added. The reaction mixture then was warmed to 50° C and stirred for 4 hours.

After cooling, the mixture was brought to pH 7 and extracted three times with 150 ml ethyl acetate.

The combined extracts were direct with anhydrous magnesium sulphate. Removal of the solvent in vacuo afforded 1,3-dicyano-2-methyl-2-hydroxypropane (56 g, 96%).

The whole amount was added carefully to a 33% solution of hydrogren bromide in glacial acetic acid at ice-bath temperature.

The reaction mixture was stirred for 3 days at ambient temperature.

The solvent was removed in vacuo and the residual brown oil brought to pH 12 with a 10 molar aqueous solution of sodium hydroxide.

The alkaline solution was extracted 3 times with 100 ml ethyl acetate. The combined extracts were dried with anhydrous magnesium sulphate and the solvent was removed in vacuo to afford 6-amino-2-bromo-4-methylpyridine (56 g, 66%) as colourless crystals. Melting point 99° C. This compound was forwarded to the next step without further purification.

To a stirred solution of 6-amino-2-bromo-4-methylpyridine (45.2 g; 0.24 mol) in 100 ml water and 43 g concentrated sulphuric acid at ice-bath temperature was given a solution of sodium nitrite (13.2 g; 0.19 mol) in 20 ml water. After 2 hours the reaction mixture was warmed to 60° C. and stirred for further 60 minutes.

After cooling, the mixture was extracted with 200 ml of dichloromethane.

The solvent was removed in vacuo and 2-bromo-4-methyl-6-hydroxypyridine (20 g, 56%) was obtained as colourless crystals of melting point 152° C.

This was mixed with 24 g phosphorylbromide in 100 ml bromoforme and heated to reflux for 3 hours.

After cooling the reaction mixture was hydrolyzed carefully with a 50% aqueous solution of sodium hydroxide and extracted 2 times with 100 ml dichloromethane. The solvent was removed in vacuo and the crude product purified by flash silica gel column chromatography using hexane/ethyl acetate 7/3. 2,6-Dibromo-4-methylpyridine (6.9 g, 25%) was obtained as a colourless solid melting point 77° C.

EXAMPLES 90 TO 99

Successive conversions according to procedures outlined in Examples 9 and 17 to 2,6-dibromo-4-methylpyridine (prepared as described in Example 89) gave compounds of the general formula XX. These are listed in table IV.

TABLE IV $$\begin{array}{c} CH_3 \\ | \\ R^1 \diagdown N \diagdown R^2 \end{array}$$

| Example No | R¹ | R² | mp (°C.) | yield (%) |
|---|---|---|---|---|
| 90 (WL396407) | 1'-Me-3'-CF₃-pyrazol-5'-yloxy | 1'-Me-3'-CF₃-pyrazol-5'-yloxy | 93 | 52 |
| 91 (CL370022) | 1'-Me-3'-CF₃-pyrazol-5'-yloxy | 3"-fluro-phenyloxy | 68 | 22 |
| 92 (CL3700223) | 1'-Me-3'-CF₃-pyrazol-5'-yloxy | 2"-fluoro-phenyloxy | 67 | 27 |
| 93 (CL370024) | 1'-Me-3'-CF₃ pyrazol-5'-yloxy | 2",4"-difluoro-phenyloxy | 84 | 21 |
| 94 (CL370025) | 1'-Me-3'-CF₃-pyrazol-5'-yloxy | 2"-methyl-phenyloxy | 91 | 11 |
| 95 (CL370026) | 1'-Me-3'-CF₃-pyrazol-5'-yloxy | 3"-chloropyrid-5"-yloxy | 64 | 20 |
| 96 (CL370029) | 1'-Me-3'-CF₃-pyrazol-5'-yloxy | phenyloxy | oil | 37 |
| 97 (CL370030) | 2'-chloropyrid-4'-yloxy | phenyloxy | oil | 17 |
| 98 (CL370031) | 2'-chloropyrid-4'-yloxy | 2"-methylphenyloxy | oil | 13 |
| 99 (WL396406) | 1'-Me-3'-CF₃-pyrazol-5'-yloxy | benzyloxy | oil | 66 |

ANALYSIS

| Example No. | C (%) calc. | C (%) found | H (%) calc. | H (%) found | N (%) calc. | N (%) found |
|---|---|---|---|---|---|---|
| 1 | 53.9 | 53.7 | 2.7 | 3.0 | 12.6 | 12.4 |
| 2A | 37.3 | 36.8 | 2.2 | 2.0 | 13.0 | 13.2 |
| 2B | 50.6 | 50.8 | 2.7 | 2.7 | 10.4 | 10.6 |
| 3A | 54.6 | 54.7 | 3.8 | 3.6 | 5.3 | 5.3 |
| 3B | 51.1 | 51.1 | 3.2 | 3.1 | 5.0 | 4.8 |
| 3C | 65.3 | 65.2 | 4.2 | 3.9 | 9.0 | 9.1 |
| ex. 4 to 8 cf Table I | | | | | | |
| 4 | 58.4 | 58.0 | 4.0 | 3.7 | 12.0 | 11.9 |
| 5 | 44.2 | 44.3 | 2.7 | 2.8 | 17.2 | 16.7 |
| 6 | 55.7 | 55.7 | 2.7 | 2.5 | 7.6 | 7.3 |
| 7 | 48.6 | 48.7 | 2.7 | 2.8 | 15.1 | 14.9 |
| 8 | 64.3 | 64.2 | 3.7 | 3.7 | 9.4 | 9.2 |

| Example No. | C (%) calc. | C (%) found | H (%) calc. | H (%) found | N (%) calc. | N (%) found |
|---|---|---|---|---|---|---|
| Example 9 | | | | | | |
| 9 | 46.0 | 45.7 | 2.7 | 2.5 | 16.1 | 16.0 |
| ex. 10 to 16 of Table II | | | | | | |
| 10 | 58.0 | 58.1 | 4.9 | 4.7 | 20.3 | 20.4 |
| 11 | 62.6 | 62.8 | 6.5 | 6.5 | 16.9 | 16.6 |
| 12 | 59.7 | 59.3 | 5.5 | 5.3 | 19.0 | 18.6 |
| 13 | 61.3 | 61.2 | 6.0 | 6.0 | 17.9 | 17.8 |
| 14 | 48.0 | 47.7 | 3.3 | 3.1 | 15.3 | 15.5 |
| 15 | 53.5 | 53.4 | 2.7 | 2.4 | 12.5 | 12.1 |
| 16 | 53.5 | 53.1 | 2.7 | 2.4 | 12.5 | 12.0 |

| Example No. | C (%) calc. | C (%) found | H (%) calc. | H (%) found | N (%) calc. | N (%) found |
|---|---|---|---|---|---|---|
| Example 17 | | | | | | |
| 17 | 57.3 | 57.1 | 3.6 | 3.8 | 12.5 | 12.3 |
| Ex. 18 to 56 cf table IIIa | | | | | | |
| 18 | 55.0 | 55.1 | 4.9 | 4.9 | 12.8 | 12.6 |
| 19 | 64.3 | 64.2 | 3.7 | 3.7 | 9.4 | 9.2 |
| 20 | 53.1 | 52.8 | 2.4 | 2.2 | 7.3 | 7.4 |
| 21 | 60.7 | 60.4 | 3.2 | 3.4 | 8.8 | 8.7 |
| 22 | 54.4 | 54.2 | 3.1 | 3.4 | 11.9 | 11.8 |
| 23 | 54.4 | 53.9 | 3.1 | 3.4 | 11.9 | 12.1 |
| 24 | 51.8 | 52.2 | 2.7 | 2.9 | 11.3 | 11.1 |
| 25 | 58.4 | 58.2 | 4.0 | 3.9 | 12.0 | 12.0 |
| 26 | 53.6 | 53.5 | 3.3 | 3.4 | 16.7 | 16.6 |
| 27 | 48.6 | 48.9 | 2.7 | 2.7 | 15.1 | 15.0 |
| 28 | 48.6 | 48.5 | 2.7 | 2.8 | 15.1 | 15.1 |
| 29 | 54.4 | 54.1 | 3.1 | 3.0 | 11.9 | 11.6 |
| 30 | 48.5 | 48.4 | 2.4 | 2.5 | 10.0 | 9.8 |
| 31 | 60.2 | 60.3 | 5.7 | 5.3 | 23.4 | 23.0 |
| 32 | 51.0 | 51.0 | 4.0 | 3.8 | 19.8 | 19.9 |
| 33 | 63.6 | 63.2 | 6.8 | 6.5 | 20.5 | 20.2 |
| 34 | 65.0 | 64.8 | 7.4 | 7.4 | 19.0 | 19.1 |
| 35 | 54.7 | 54.7 | 5.1 | 5.1 | 17.7 | 17.6 |
| 36 | 62.4 | 62.2 | 6.5 | 6.5 | 21.4 | 21.2 |
| 37 | 62.4 | 62.0 | 6.5 | 6.4 | 21.4 | 21.3 |
| 38 | 53.5 | 53.4 | 4.8 | 4.8 | 18.4 | 18.1 |
| 39 | 64.2 | 64.4 | 7.1 | 7.0 | 19.7 | 19.7 |
| 40 | 65.8 | 65.9 | 7.6 | 7.6 | 18.3 | 18.1 |
| 41 | 60.2 | 60.2 | 5.3 | 5.4 | 15.6 | 15.6 |
| 42 | 66.8 | 66.5 | 5.9 | 6.0 | 12.3 | 12.2 |
| 43 | 66.8 | 66.7 | 5.9 | 5.8 | 12.3 | 12.4 |
| 44 | 66.8 | 66.7 | 5.9 | 5.7 | 12.3 | 12.3 |
| 45 | 65.3 | 65.3 | 4.2 | 4.0 | 9.0 | 8.8 |
| 46 | 60.7 | 60.8 | 3.2 | 3.2 | 8.8 | 9.0 |
| 47 | 60.7 | 60.9 | 3.2 | 3.3 | 8.8 | 8.8 |
| 48 | 53.9 | 53.7 | 2.7 | 2.9 | 12.6 | 12.5 |
| 49 | 59.5 | 59.5 | 4.4 | 4.3 | 11.6 | 11.6 |
| 50 | 53.2 | 52.9 | 3.4 | 3.2 | 10.9 | 10.6 |
| 51 | 56.4 | 56.5 | 3.6 | 3.6 | 15.5 | 15.2 |
| 52 | 47.5 | 47.6 | 2.5 | 2.3 | 10.4 | 10.4 |
| 53 | 46.6 | 46.6 | 2.3 | 2.4 | 9.6 | 9.4 |
| 54 | 56.7 | 56.6 | 3.1 | 2.8 | 15.5 | 15.5 |
| 55 | 51.7 | 51.8 | 2.6 | 2.6 | 14.2 | 14.0 |
| 56 | 49.6 | 49.5 | 2.6 | 2.4 | 10.8 | 11.0 |

| Example No. | C (%) calc. | C (%) found | H (%) calc. | H (%) found | N (%) calc. | N (%) found |
|---|---|---|---|---|---|---|
| Ex. 57 to 85 cf. table IIIb | | | | | | |
| 57 | 55.6 | 55.9 | 3.6 | 3.6 | 11.4 | 11.2 |
| 58 | 55.6 | 55.5 | 3.6 | 3.3 | 11.4 | 11.0 |
| 59 | 55.6 | 55.4 | 3.6 | 3.3 | 11.4 | 11.2 |
| 60 | 51.8 | 51.8 | 3.1 | 3.0 | 10.1 | 9.9 |
| 61 | 51.8 | 51.5 | 3.1 | 3.0 | 10.1 | 10.1 |
| 62 | 59.5 | 59.4 | 4.4 | 4.6 | 11.6 | 11.5 |
| 63 | 59.5 | 59.5 | 4.4 | 4.5 | 11.6 | 11.5 |
| 64 | 62.2 | 62.3 | 5.5 | 5.3 | 10.4 | 10.4 |
| 65 | 53.2 | 53.2 | 3.4 | 3.5 | 11.0 | 10.8 |
| 66 | 59.5 | 59.4 | 4.4 | 4.4 | 11.6 | 11.3 |
| 67 | 48.8 | 49.2 | 2.9 | 2.9 | 10.1 | 10.3 |
| 68 | 59.5 | 59.5 | 4.4 | 4.1 | 11.6 | 11.2 |
| 69 | 53.2 | 53.0 | 3.4 | 3.3 | 11.0 | 11.0 |
| 70 | 53.2 | 53.3 | 3.4 | 3.4 | 11.0 | 10.8 |
| 71 | 53.0 | 52.7 | 3.1 | 3.0 | 10.9 | 11.0 |
| 72 | 50.6 | 50.6 | 2.7 | 2.9 | 10.4 | 10.3 |
| 73 | 50.6 | 50.1 | 2.7 | 2.4 | 10.4 | 10.7 |
| 74 | 61.7 | 61.7 | 3.7 | 3.4 | 8.5 | 8.1 |
| 75 | 51.8 | 51.6 | 3.1 | 3.1 | 10.1 | 10.0 |
| 76 | 71.8 | 71.5 | 7.2 | 6.9 | 12.0 | 11.8 |
| 77 | 61.7 | 61.8 | 3.7 | 3.7 | 8.5 | 8.4 |
| 78 | 61.7 | 61.7 | 3.7 | 3.7 | 8.5 | 8.3 |
| 79 | 66.2 | 66.0 | 4.6 | 4.7 | 8.6 | 8.6 |
| 80 | 58.5 | 58.0 | 3.2 | 2.8 | 8.0 | 8.3 |
| 81 | 67.6 | 67.5 | 6.2 | 6.0 | 11.8 | 11.7 |
| 82 | 67.6 | 68.0 | 6.2 | 6.2 | 11.8 | 11.8 |
| 83 | 67.6 | 67.7 | 6.2 | 6.3 | 11.8 | 11.8 |
| 84 | 64.3 | 64.3 | 5.7 | 5.4 | 11.2 | 11.0 |
| 85 | 71.2 | 71.4 | 6.9 | 6.9 | 12.4 | 12.0 |

| Example No. | C (%) calc. | C (%) found | H (%) calc. | H (%) found | N (%) calc. | N (%) found |
|---|---|---|---|---|---|---|
| Ex. 86 to 88 cf. table IIIc | | | | | | |
| 86 | 59.5 | 59.4 | 4.4 | 4.2 | 11.6 | 11.6 |
| 87 | 52.5 | 52.5 | 3.4 | 3.6 | 14.1 | 14.0 |
| 88 | 53.3 | 53.0 | 5.1 | 5.2 | 13.3 | 13.3 |

Example 89

| Example No. | C (%) calc. | C (%) found | H (%) calc. | H (%) found | N (%) calc. | N (%) found |
|---|---|---|---|---|---|---|
| 89 | 28.7 | 28.7 | 2.0 | 1.8 | 5.6 | 5.8 |

Ex. 90 to 99 cf. table IV

| | | | | | | |
|---|---|---|---|---|---|---|
| 90 | 55.0 | 54.8 | 4.9 | 4.8 | 12.8 | 12.8 |
| 91 | 55.6 | 55.6 | 3.6 | 3.7 | 11.4 | 11.2 |
| 92 | 55.6 | 55.3 | 3.6 | 3.4 | 11.4 | 11.3 |
| 93 | 53.0 | 52.6 | 3.1 | 3.0 | 10.9 | 10.9 |
| 94 | 59.5 | 59.5 | 4.4 | 4.2 | 11.6 | 11.5 |
| 95 | 49.9 | 50.0 | 3.1 | 3.1 | 14.6 | 14.4 |
| 96 | 58.5 | 58.1 | 4.0 | 3.8 | 12.0 | 11.9 |
| 97 | 65.3 | 65.4 | 4.2 | 3.9 | 9.0 | 8.8 |
| 98 | 66.2 | 66.1 | 4.6 | 4.2 | 8.6 | 8.6 |
| 99 | 59.5 | 59.2 | 4.4 | 4.1 | 11.6 | 11.4 |

EXAMPLE 100
Herbicidal Activity

To evaluate their herbicidal activity, compounds according to the invention were tested using as representative range of plants: maize, *Zea mays* (Mz); rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant specied mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 litres per hectare in the soil spray and foliar spray test, and at a dosage of level equivalent to 10 kilograms of active material per hectare in a volume equivalent to approximately 3,000 litres per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table III below, in which the compounds are identified by reference to the preceding examples. Absence of a numeral in the Table indicates a zero rating, an asterisk indicates that no result was obtained.

TABLE V

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | K | SB | S | | Mz | R | BG | O | L | M | SB | S | Mz | R | BG | O | L | M | SB | S |
| 1 | 6 | 2 | 8 | 5 | 6 | 7 | 7 | 4 | 5 | 4 | 2 | 8 | 5 | 8 | 8 | 8 | 6 | 4 | 0 | 6 | 4 | 4 | 8 | 8 | 4 |
| | | | | | | | | | 1 | 2 | 0 | 7 | 2 | 7 | 8 | 8 | 6 | 2 | 0 | 5 | 0 | 2 | 7 | 8 | 2 |
| 2 | 6 | 6 | 8 | 7 | 5 | 8 | 8 | 4 | 5 | 6 | 6 | 8 | 7 | 6 | 8 | 9 | 8 | 6 | 5 | 9 | 7 | 7 | 8 | 9 | 6 |
| | | | | | | | | | 1 | 5 | 4 | 8 | 6 | 5 | 8 | 9 | 8 | 2 | 2 | 8 | 6 | 7 | 8 | 8 | 5 |
| 3 | 6 | 7 | 8 | 5 | 2 | 7 | 6 | 1 | 5 | 7 | 7 | 8 | 7 | 8 | 9 | 9 | 8 | 6 | 6 | 9 | 7 | 7 | 9 | 9 | 7 |
| | | | | | | | | | 1 | 6 | 6 | 7 | 6 | 8 | 9 | 9 | 8 | 6 | 5 | 9 | 6 | 7 | 9 | 9 | 6 |
| 4 | 6 | 7 | 8 | 7 | 4 | 9 | 7 | 1 | 5 | 8 | 7 | 8 | 7 | 8 | 9 | 9 | 8 | 7 | 7 | 9 | 8 | 9 | 9 | 9 | 8 |
| | | | | | | | | | 1 | 7 | 6 | 8 | 7 | 8 | 9 | 9 | 8 | 6 | 5 | 9 | 8 | 8 | 9 | 9 | 7 |
| 5 | * | * | * | * | * | * | * | * | 5 | 6 | 7 | 8 | 7 | 8 | 8 | 9 | 8 | 6 | 4 | 9 | 7 | 9 | 8 | 9 | 7 |
| | | | | | | | | | 1 | 6 | 5 | 8 | 7 | 8 | 8 | 6 | 8 | 5 | 2 | 9 | 7 | 9 | 8 | 9 | 6 |
| 6 | 7 | 4 | 7 | 6 | 2 | 5 | 6 | 0 | 5 | 7 | 5 | 8 | 7 | 8 | 8 | 9 | 7 | 5 | 7 | 8 | 4 | 5 | 7 | 6 | 2 |
| | | | | | | | | | 1 | 6 | 4 | 6 | 7 | 8 | 8 | 9 | 6 | 2 | 2 | 5 | 1 | 2 | 4 | 5 | 0 |
| 7 | 7 | 7 | 8 | 7 | 6 | 8 | 8 | 4 | 5 | 7 | 6 | 8 | 8 | 7 | 9 | 9 | 8 | 5 | 6 | 8 | 6 | 7 | 8 | 9 | 6 |
| | | | | | | | | | 1 | 6 | 5 | 8 | 7 | 7 | 9 | 9 | 8 | 4 | 2 | 8 | 5 | 6 | 8 | 8 | 5 |
| 8 | 0 | 0 | 3 | 0 | 0 | 4 | 3 | 0 | 5 | 2 | 1 | 8 | 6 | 5 | 7 | 9 | 2 | 0 | 0 | 0 | 0 | 0 | 0 | 0 | 0 |
| | | | | | | | | | 1 | 0 | 0 | 7 | 0 | 2 | 6 | 6 | 1 | 0 | 0 | 0 | 0 | 0 | 0 | 0 | 0 |

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | MZ | R | BG | O | L | K | SB | S | | Mz | R | BG | O | L | M | SB | S | MZ | R | BG | O | L | M | SB | S |
| 18 | | | | | | | | | 5 | * | * | * | * | * | * | * | * | * | * | * | * | * | * | * | * |
| | * | * | * | * | * | * | * | | 1 | 4 | 2 | 6 | 4 | 4 | 8 | 6 | 5 | 1 | 1 | 2 | 3 | 0 | 6 | 2 | 0 |
| 19 | 0 | 0 | 3 | 0 | 0 | 4 | 3 | 0 | 5 | 2 | 1 | 8 | 6 | 5 | 7 | 9 | 2 | 0 | 0 | 0 | 0 | 0 | 0 | 0 | 0 |
| | | | | | | | | | 1 | 0 | 0 | 7 | 0 | 2 | 6 | 6 | 1 | 0 | 0 | 0 | 0 | 0 | 0 | 0 | 0 |
| 20 | 5 | 4 | 7 | 6 | 3 | 5 | 6 | 4 | 5 | 7 | 5 | 8 | 7 | 8 | 9 | 9 | 8 | 6 | 5 | 8 | 7 | 5 | 8 | 9 | 6 |
| | | | | | | | | | 1 | 7 | 4 | 8 | 6 | 8 | 9 | 9 | 8 | 6 | 4 | 8 | 6 | 4 | 7 | 9 | 5 |
| 21 | 0 | 0 | 0 | 0 | 0 | 0 | 0 | 0 | 5 | 0 | 0 | 0 | 0 | 0 | 8 | 6 | 3 | 0 | 0 | 0 | 0 | 0 | 0 | 0 | 0 |
| | | | | | | | | | 1 | 0 | 0 | 0 | 0 | 0 | 6 | 4 | 0 | 0 | 0 | 0 | 0 | 0 | 0 | 0 | 0 |
| 57 | 6 | 8 | 8 | 7 | 7 | 9 | 9 | 6 | 5 | 8 | 8 | 8 | 7 | 8 | 9 | 9 | 8 | 6 | 7 | 9 | 8 | 8 | 9 | 9 | 8 |
| | | | | | | | | | 1 | 7 | 5 | 8 | 6 | 8 | 9 | 9 | 8 | 5 | 2 | 9 | 8 | 8 | 9 | 9 | 7 |

TABLE V-continued

| No. | | | | | | | | | Dose | | | | | | | | | | | | | | | | |
|---|---|---|---|---|---|---|---|---|---|---|---|---|---|---|---|---|---|---|---|---|---|---|---|---|---|
| 58 | 8 | 7 | 8 | 8 | 7 | 8 | 9 | 5 | 5 | 8 | 7 | 8 | 7 | 7 | 9 | 9 | 8 | 7 | 7 | 9 | 9 | 8 | 9 | 9 | 7 |
|    |   |   |   |   |   |   |   |   | 1 | 7 | 6 | 8 | 7 | 7 | 8 | 9 | 8 | 6 | 5 | 9 | 8 | 7 | 9 | 9 | 6 |
| 59 | 4 | 3 | 7 | 7 | 6 | 8 | 9 | 3 | 5 | 7 | 6 | 8 | 7 | 7 | 8 | 9 | 8 | 6 | 6 | 9 | 8 | 7 | 9 | 9 | 5 |
|    |   |   |   |   |   |   |   |   | 1 | 6 | 5 | 8 | 6 | 7 | 8 | 9 | 8 | 5 | 4 | 9 | 7 | 6 | 9 | 9 | 4 |
| 60 | 3 | 0 | 6 | 4 | 3 | 8 | 6 | 2 | 5 | 7 | 4 | 8 | 7 | 7 | 9 | 9 | 8 | 4 | 0 | 9 | 7 | 5 | 9 | 9 | 3 |
|    |   |   |   |   |   |   |   |   | 1 | 6 | 2 | 7 | 6 | 7 | 8 | 9 | 8 | 3 | 0 | 8 | 6 | 4 | 9 | 9 | 2 |
| 61 | 2 | 0 | 6 | 5 | 4 | 8 | 8 | 2 | 5 | 7 | 5 | 8 | 8 | 8 | 9 | 9 | 8 | 5 | 0 | 9 | 8 | 6 | 9 | 9 | 2 |
|    |   |   |   |   |   |   |   |   | 1 | 6 | 4 | 7 | 7 | 7 | 8 | 9 | 7 | 4 | 0 | 7 | 8 | 6 | 9 | 9 | 0 |
| 62 | 3 | 0 | 6 | 5 | 7 | 8 | 8 | 4 | 5 | 6 | 6 | 8 | 7 | 7 | 8 | 9 | 8 | 5 | 0 | 9 | 8 | 7 | 9 | 9 | 4 |
|    |   |   |   |   |   |   |   |   | 1 | 5 | 5 | 6 | 5 | 7 | 7 | 9 | 7 | 4 | 0 | 9 | 5 | 6 | 9 | 9 | 3 |
| 63 | 6 | 5 | 7 | 4 | 7 | 8 | 8 | 6 | 5 | 7 | 6 | 8 | 7 | 7 | 8 | 9 | 8 | 6 | 5 | 9 | 8 | 8 | 9 | 9 | 7 |
|    |   |   |   |   |   |   |   |   | 1 | 6 | 5 | 8 | 7 | 7 | 8 | 9 | 8 | 5 | 4 | 9 | 7 | 8 | 9 | 9 | 6 |
| 64 | 2 | 0 | 5 | 1 | 4 | 7 | 6 | 2 | 5 | 7 | 2 | 8 | 7 | 7 | 9 | 9 | 7 | 0 | 0 | 7 | 2 | 0 | 7 | 5 | 2 |
|    |   |   |   |   |   |   |   |   | 1 | 7 | 0 | 7 | 6 | 7 | 8 | 9 | 7 | 0 | 0 | 5 | 0 | 0 | 5 | 4 | 0 |
| 65 | 6 | 2 | 8 | 7 | 5 | 7 | 9 | 2 | 5 | 8 | 6 | 8 | 6 | 7 | 9 | 9 | 8 | 6 | 3 | 9 | 6 | 4 | 9 | 9 | 4 |
|    |   |   |   |   |   |   |   |   | 1 | 7 | 5 | 8 | 6 | 7 | 9 | 9 | 7 | 4 | 0 | 8 | 5 | 2 | 9 | 8 | 0 |
| 66 | 4 | 0 | 5 | 4 | 3 | 7 | 8 | 0 | 5 | 6 | 4 | 8 | 7 | 7 | 9 | 9 | 7 | 5 | 0 | 9 | 6 | 4 | 9 | 9 | 2 |
|    |   |   |   |   |   |   |   |   | 1 | 5 | 2 | 7 | 6 | 7 | 8 | 9 | 6 | 2 | 0 | 8 | 5 | 3 | 8 | 8 | 0 |
| 67 | 0 | 0 | 0 | 0 | 0 | 0 | 0 | 0 | 5 | 5 | 0 | 5 | 4 | 6 | 8 | 9 | 5 | 0 | 0 | 0 | 0 | 0 | 0 | 0 | 0 |
|    |   |   |   |   |   |   |   |   | 1 | 4 | 0 | 5 | 1 | 4 | 8 | 8 | 4 | 0 | 0 | 0 | 0 | 0 | 0 | 0 | 0 |
| 68 | 0 | 0 | 0 | 0 | 0 | 0 | 0 | 0 | 5 | 5 | 5 | 5 | 4 | 5 | 9 | 8 | 5 | 2 | 0 | 4 | 0 | 0 | 6 | 2 | 0 |
|    |   |   |   |   |   |   |   |   | 1 | 4 | 4 | 2 | 2 | 4 | 7 | 8 | 4 | 0 | 0 | 2 | 0 | 0 | 5 | 0 | 0 |
| 69 | 6 | 6 | 8 | 7 | 5 | 8 | 8 | 2 | 5 | 8 | 7 | 8 | 7 | 8 | 9 | 9 | 8 | 6 | 7 | 9 | 8 | 6 | 9 | 9 | 6 |
|    |   |   |   |   |   |   |   |   | 1 | 7 | 6 | 8 | 7 | 8 | 9 | 9 | 7 | 6 | 5 | 9 | 7 | 5 | 9 | 9 | 5 |
| 70 | 6 | 5 | 8 | 5 | 5 | 7 | 6 | 3 | 5 | 7 | 6 | 8 | 7 | 7 | 9 | 9 | 8 | 5 | 6 | 9 | 7 | 7 | 9 | 9 | 6 |
|    |   |   |   |   |   |   |   |   | 1 | 6 | 5 | 8 | 5 | 7 | 9 | 9 | 8 | 5 | 5 | 9 | 6 | 6 | 9 | 9 | 5 |
| 71 | * | * | * | * | * | * | * | * | 5 |   | 5 | 7 | 7 | 8 | 9 | 9 |   |   | 6 | 9 | 6 | 5 | 8 | 9 |   |
|    |   |   |   |   |   |   |   |   | 1 |   | 2 | 6 | 5 | 7 | 7 | 8 |   |   | 2 | 8 | 6 | 4 | 8 | 9 |   |
| 72 | 8 | 7 | 8 | 7 | 5 | 6 | 4 | 7 | 5 | 7 | 6 | 8 | 8 | 8 | 9 | 9 | 8 | 6 | 5 | 9 | 9 | 8 | 9 | 9 | 7 |
|    |   |   |   |   |   |   |   |   | 1 | 7 | 5 | 8 | 8 | 7 | 9 | 9 | 8 | 6 | 5 | 8 | 8 | 8 | 8 | 9 | 6 |
| 73 | 4 | 5 | 7 | 4 | 3 | 5 | 6 | 4 | 5 | 6 | 4 | 8 | 8 | 8 | 9 | 9 | 8 | 6 | 4 | 9 | 8 | 7 | 8 | 9 | 7 |
|    |   |   |   |   |   |   |   |   | 1 | 5 | 2 | 8 | 7 | 7 | 9 | 9 | 8 | 5 | 2 | 8 | 7 | 6 | 8 | 8 | 4 |
| 74 | * | * | * | * | * | * | * | * | 5 | 7 | 5 | 8 | 7 | 8 | 9 | 9 | 8 | 5 | 5 | 9 | 7 | 5 | 8 | 9 | 2 |
|    |   |   |   |   |   |   |   |   | 1 | * | * | * | * | * | * | * | * | * | * | * | * | * | * | * |
| 86 | 6 | 0 | 7 | 4 | 6 | 8 | 9 | 4 | 5 | 7 | 6 | 8 | 8 | 7 | 9 | 9 | 8 | 4 | 3 | 9 | 7 | 4 | 8 | 8 | 3 |
|    |   |   |   |   |   |   |   |   | 1 | 7 | 5 | 8 | 7 | 6 | 8 | 8 | 7 | 2 | 0 | 8 | 4 | 2 | 8 | 7 | 0 |
| 90 | 6 | 5 | 7 | 7 | 4 | 7 | 5 | 3 | 5 | 6 | 7 | 8 | 7 | 8 | 8 | 9 | 8 | 4 | 5 | 9 | 7 | 8 | 9 | 9 | 6 |
|    |   |   |   |   |   |   |   |   | 1 | 6 | 5 | 8 | 7 | 7 | 9 | 9 | 8 | 3 | 0 | 8 | 7 | 7 | 8 | 9 | 5 |
| 99 | 5 | 4 | 8 | 7 | 5 | 7 | 7 | 3 | 5 | 7 | 5 | 8 | 8 | 8 | 9 | 9 | 8 | 6 | 5 | 9 | 8 | 8 | 9 | 9 | 7 |
|    |   |   |   |   |   |   |   |   | 1 | 7 | 5 | 7 | 7 | 7 | 8 | 9 | 8 | 6 | 5 | 9 | 8 | 8 | 9 | 9 | 7 |

I claim:

1. A method of combating undesired plant growth at a locus which comprises treating the locus with a 2,6-substituted pyridine of the formula 1:

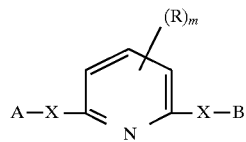

wherein X represents an oxygen or sulphur atom, A represents an optionally substituted 5 or 6 membered nitrogen-containing heteroaromatic group; B represents an optionally substituted 5 or 6 membered cyclic hydrocarbon, alkyl, alkenyl, alkynyl, aryl or aralkyl group, or one of the meanings for A; R represents a halogen atom or an alkyl, haloalkyl, alkoxy, alkylthio or dialkylamino group; and m represents 0, 1 or 2.

2. A method as claimed in claim 1 wherein A represents a pyridyl or pyrazolyl group optionally substituted with a halogen atom or an alkyl or haloalkyl group.

3. A method as claimed in claim 2 wherein B represents a phenyl, benzyl, pyridyl or pyrazolyl group optionally substituted with a halogen atom or an alkyl or haloalkyl group.

4. A method as claimed in claim 2 wherein each of A and B, except when B is aralkyl, has a substituent at the 3 position.

5. A method as claimed in claim 4 wherein each of A and B is substituted by a chlorine atom, a methyl group or a trifluoromethyl group.

6. A method as claimed in claim 5 wherein A represents a 2-chloro pyrid-4-yl or 1-methyl-3-trifluoromethyl pyrazol-5-yl group, and B represents a 3-trifluoromethylphenyl or a benzyl group or one of the meanings for A.

7. A method as claimed in claim 1 wherein X is oxygen and m is 0.

8. A method for combating undesired plant growth at a locus comprising applying a herbicidally effective amount of a compound as defined in claim 1 to the locus.

9. A compound of formula I as defined in claim 1, wherein X, A, R, and m have the meaning given in claim 1 and B represents an optionally substituted 5 or 6 membered cyclic hydrocarbon, aryl, or aralkyl group, or one of the meanings of A, with the proviso that the following compounds are excluded:

2,6-bis[(6-bromo-2-pyridinyl)thio]pyridine; 2,2'-thiobis[6-[(6-bromo-2-pyridinyl)thio]]pyridine;
2,6-bis{[6-[(6-bromo-2-pyridinyl)thio]-2-pyridinyl]thio}pyridine; 2,2'-thiobis[6-{[6-[(6-bromo-2-pyridinyl)thio]]-2-pyridinyl}thio]pyridine; and 2,6-bis[(1-methyl-1H-imidazol-2-yl)thio]pyridine.

10. Process for the preparation of compounds as claimed in claim 9 wherein A and B are the same which comprises reacting a 2,6-dihalopyridine of formula II

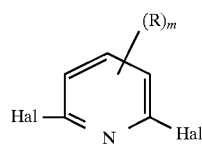

(II)

with at least a twofold molar excess of a metal salt of an alcohol or thiol of formula AXH, the symbols R, A, X and m having the meanings defined in claim 1 and Hal denoting a halogen atom.

11. Process for the preparation of compounds as claimed in claim 9 wherein group B is different from group A, which comprises reacting a 2,6-dihalopyridine of formula II with at most an equimolar amount of a metal salt of an alcohol or thiol of formula AXH, followed by further reaction with at least an equimolar amount of a metal salt of an alcohol or thiol of formula BXH.

12. Process as claimed in claim 11 in which the reaction(s) is carried in a polar organic solvent.

13. Process as claimed in claim 12 in which an alkali metal salt of the alcohol or thiol is reacted at elevated temperature with the dihalopyridine.

14. Process for the preparation of compounds as claimed in claim 9 wherein group B is different from group A, which comprises reacting a halopyridone of formula III

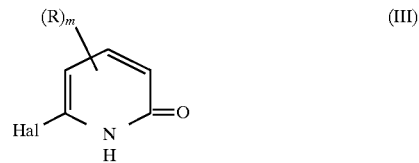

(III)

with a halide of formula B Hal, wherein each Hal denotes a halogen atom, followed by reaction with a metal salt of an alcohol or thiol of formula AXH.

15. A 2,6-dihalopyridine compound prepared by a process as claimed in claim 10.

16. A herbicidal composition which comprises a compound as defined in claim 9 and a herbically acceptable carrier or a surface-active agent, or a combination thereof.

* * * * *